US012611656B2

(12) United States Patent
Lim et al.

(10) Patent No.: US 12,611,656 B2
(45) **Date of Patent: *Apr. 28, 2026**

(54) MANUFACTURING METHOD FOR MOLYBDENUM-BISMUTH COMPOSITE METAL OXIDE

(71) Applicant: LG CHEM, LTD., Seoul (KR)

(72) Inventors: Hyunsub Lim, Daejeon (KR); Byung Yul Choi, Daejeon (KR); Young Hyun Choe, Daejeon (KR); Dong Woo Seo, Daejeon (KR); Hyeonho Joo, Daejeon (KR); Youngju Choi, Daejeon (KR); Saeha Lee, Daejeon (KR); Minsu Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 840 days.

This patent is subject to a terminal disclaimer.

(21) Appl. No.: 17/781,651

(22) PCT Filed: Aug. 17, 2021

(86) PCT No.: PCT/KR2021/010873

§ 371 (c)(1),
(2) Date: Jun. 1, 2022

(87) PCT Pub. No.: WO2022/080642

PCT Pub. Date: Apr. 21, 2022

(65) Prior Publication Data

US 2023/0001390 A1 Jan. 5, 2023

(30) Foreign Application Priority Data

Oct. 16, 2020 (KR) ........................ 10-2020-0134276

(51) Int. Cl.

| | |
|---|---|
| ***B01J 37/04*** | (2006.01) |
| ***B01J 23/887*** | (2006.01) |
| ***B01J 35/40*** | (2024.01) |
| ***B01J 37/02*** | (2006.01) |
| ***B01J 37/03*** | (2006.01) |
| ***B01J 37/08*** | (2006.01) |
| ***C07C 51/25*** | (2006.01) |

(52) U.S. Cl.

CPC ........... *B01J 23/8876* (2013.01); *B01J 35/40* (2024.01); *B01J 37/0236* (2013.01); *B01J 37/038* (2013.01); *B01J 37/04* (2013.01); *B01J 37/088* (2013.01); *C07C 51/252* (2013.01)

(58) Field of Classification Search

CPC .. B01J 23/8876; B01J 37/0236; B01J 37/038; B01J 37/04; B01J 37/088; C07C 51/252

See application file for complete search history.

(56) References Cited

U.S. PATENT DOCUMENTS

| | | | | |
|---|---|---|---|---|
| 4,212,766 | A | 7/1980 | Brazdil et al. | |
| 6,777,369 | B1 | 8/2004 | Kuroda et al. | |
| 2003/0191344 | A1 | 10/2003 | Yunoki | |
| 2007/0032679 | A1 | 2/2007 | Naitou et al. | |
| 2009/0171117 | A1 | 7/2009 | Arnold et al. | |
| 2011/0092734 | A1 | 4/2011 | Hagemeyer et al. | |
| 2013/0172615 | A1 | 7/2013 | Kawano et al. | |
| 2014/0316160 | A1 | 10/2014 | Iijima et al. | |
| 2015/0080210 | A1 | 3/2015 | Chun et al. | |
| 2016/0001270 | A1 | 1/2016 | Lim et al. | |
| 2016/0184805 | A1* | 6/2016 | Xiong et al. | B01J 23/887 |
| 2018/0184805 | A1 | 7/2018 | Lambert | |
| 2018/0186712 | A1 | 7/2018 | Sugiyama et al. | |
| 2018/0222850 | A1 | 8/2018 | Li et al. | |
| 2019/0060884 | A1 | 2/2019 | Choi et al. | |
| 2021/0078929 | A1 | 3/2021 | Wen et al. | |
| 2021/0322959 | A1 | 10/2021 | Tomoda et al. | |

FOREIGN PATENT DOCUMENTS

| | | | |
|---|---|---|---|
| CN | 105026036 | A | 11/2015 |
| CN | 109985649 | A | 7/2019 |
| CN | 110214054 | A | 9/2019 |
| EP | 3950122 | | 2/2022 |
| KR | 10-2002-0010659 | A | 2/2002 |
| KR | 10-2006-0076320 | A | 7/2006 |
| KR | 10-0660988 | | 12/2006 |
| KR | 10-2010-0134091 | A | 12/2010 |
| KR | 10-2015-0014085 | A | 2/2015 |
| KR | 10-2015-0053723 | A | 5/2015 |
| KR | 10-2018-0055154 | A | 5/2018 |
| KR | 10-2019-0003830 | A | 1/2019 |
| KR | 10-2020-0090314 | A | 7/2020 |
| WO | 2019-198401 | A1 | 10/2019 |
| WO | 2020203606 | | 10/2020 |

OTHER PUBLICATIONS

Environ. Prog. 2005, 24, 181-197 (Srivastava) (Year: 2005).*

* cited by examiner

*Primary Examiner* — Amy C Bonaparte
*Assistant Examiner* — Derek Rhoades
(74) *Attorney, Agent, or Firm* — Bryan Cave Leighton Paisner LLP

(57) ABSTRACT

A method for preparing a molybdenum-bismuth-based composite metal oxide.

6 Claims, No Drawings

MANUFACTURING METHOD FOR MOLYBDENUM-BISMUTH COMPOSITE METAL OXIDE

CROSS-REFERENCE TO RELATED APPLICATIONS

This application is a US national phase of international application No. PCT/KR2021/010873 filed Aug. 17, 2021, and claims priority to and the benefits of Korean Patent Application No. 10-2020-0134276, filed with the Korean Intellectual Property Office on Oct. 16, 2020, the entire contents of which are incorporated herein by reference.

TECHNICAL FIELD

The present application relates to a method for preparing a molybdenum-bismuth-based composite metal oxide.

BACKGROUND

In the preparation of (meth)acrolein and/or (meth)acrylic acid, a gas-phase catalytic oxidation of propylene, isobutylene or the like with molecular oxygen in a fixed bed multi-tubular reactor having a catalyst layer present therein is generally used.

The reaction is divided into a first step reaction zone in which propylene, isobutylene or the like is partially oxidized to prepare (meth)acrolein, and a second step reaction zone in which the (meth)acrolein is partially oxidized to prepare (meth)acrylic acid.

The first step reaction zone and the second step reaction zone are provided with a first catalyst layer and a second catalyst layer, respectively, and a molybdenum-bismuth-based composite metal oxide is used as a catalyst in the catalyst layer.

The molybdenum-bismuth-based composite metal oxide is generally prepared by co-precipitating and calcining a precursor compound of each metal, and a nitric acid salt or an ammonium salt is mainly used as the precursor compound.

There are problems associated with the above-described method, including disposing ammonia and NOx substances generated from the nitric acid salt and the ammonium salt used in the process, equipment corrosion caused by the same, occupational exposure to workers, and the like, and thus, there has been a need to change the type of the precursor compound.

RELEVANT PATENT DOCUMENT

KR 10-2014-0062552 A

SUMMARY

One exemplary embodiment of the present disclosure is directed to a method for preparing a molybdenum-bismuth-based composite metal oxide having a reduced amount of nitric acid or ammonia generated during the preparation process.

One exemplary embodiment of the present disclosure provides a method for preparing a molybdenum-bismuth-based composite metal oxide represented by Chemical Formula 1, the method including preparing a catalyst suspension comprising: a molybdenum-based compound, a bismuth-based compound, an $M^2$-based compound, an $M^3$-based compound and an $M^6$-based compound; and drying the catalyst suspension, wherein any one of more of the molybdenum-based compound, the bismuth-based compound, the $M^2$-based compound, the $M^3$-based compound and the $M^6$-based compound are an oxide or hydrate of each element. The catalyst suspension optionally further comprising one or more of: an $M^1$-based compound, an $M^4$-based compound, and an $M^5$-based compound.

[Chemical Formula 1]

$$Mo_aBi_bM^1_cM^2_dM^3_eM^4_fM^5_gM^6_hO_i,$$

and in Chemical Formula 1,

Mo is molybdenum,

Bi is bismuth, $M^1$ is one or more selected from the group consisting of W, Sb, As, P, Sn and Pb, $M^2$ is one or more selected from the group consisting of Fe, Zn, Cr, Mn, Cu, Pd, Ag and Ru, $M^3$ is one or more selected from the group consisting of Co, Cd, Ta, Pt and Ni, $M^4$ is one or more selected from the group consisting of Al, Zr, V and Ce, $M^5$ is one or more selected from the group consisting of Se, Ga, Ti, Ge, Rh and Au, $M^6$ is one or more selected from the group consisting of Na, K, Li, Rb, Cs, Ca, Mg, Sr and Ba, a, b, c, d, e, f, g, h and i represent an atomic ratio of each element, and when a=12, b is from 0.01 to 20, c is from 0 to 20, d is from 0.001 to 15, e is from 0.001 to 20, f is from 0 to 20, g is from 0 to 10, h is from 0.001 to 10, and i is a numerical value determined by an oxidation state of each component.

In addition, one exemplary embodiment of the present disclosure provides a method for preparing (meth)acrylic acid using a fixed bed reactor including a front-end catalyst layer and a rear-end catalyst layer, the method including preparing (meth)acrolein by supplying an injection gas including a raw material gas, which includes propylene, isobutylene or a mixture thereof, and oxygen gas to the front-end catalyst layer; and preparing (meth)acrylic acid by supplying the (meth) acrolein to the rear-end catalyst layer, wherein the molybdenum-bismuth-based composite metal oxide prepared using the above-described preparation method is included in the front-end catalyst layer or the rear-end catalyst layer.

According to a method for preparing a molybdenum-bismuth-based composite metal oxide according to one exemplary embodiment of the present disclosure, the amount of nitric acid and ammonia generated when preparing a catalyst can be reduced.

DETAILED DESCRIPTION

Hereinafter, the present disclosure will be described in detail.

Known methods for preparing molybdenum-bismuth-based composite metal oxide include co-precipitating and calcining a precursor compound of each metal element using a nitric acid salt or an ammonium salt mainly as the precursor compound. A problem associated with such methods includes discharging large amounts of ammonia and NOx substances generated by the nitric acid salt and the ammonium salt.

The inventors of the present disclosure have identified that generation of ammonia and NOx substances may be minimized by changing the type of the metal precursor material, and have completed the present disclosure.

Specifically, one exemplary embodiment of the present disclosure provides a method for preparing a molybdenum-bismuth-based composite metal oxide represented by Chemical Formula 1, the method including preparing a catalyst suspension comprising a molybdenum-based compound, a bismuth-based compound, an $M^2$-based compound, an $M^3$-based compound and an $M^6$-based compound; and drying the catalyst suspension, wherein any one of more of the molybdenum-based compound, the bismuth-based compound, the $M^2$-based compound, the $M^3$-based compound and the $M^6$-based compound are an oxide or hydrate of each element. The catalyst suspension optionally further comprising one or more of: an $M^1$-based compound, an $M^4$-based compound, and an $M^5$-based compound.

[Chemical Formula 1]

$$Mo_aBi_bM^1_cM^2_dM^3_eM^4_fM^5_gM^6_hO_i,$$

in Chemical Formula 1,

Mo is molybdenum,

Bi is bismuth, $M^1$ is one or more selected from the group consisting of W, Sb, As, P, Sn and Pb, $M^2$ is one or more selected from the group consisting of Fe, Zn, Cr, Mn, Cu, Pd, Ag and Ru, $M^3$ is one or more selected from the group consisting of Co, Cd, Ta, Pt and Ni, $M^4$ is one or more selected from the group consisting of Al, Zr, V and Ce, $M^5$ is one or more selected from the group consisting of Se, Ga, Ti, Ge, Rh and Au, $M^6$ is one or more selected from the group consisting of Na, K, Li, Rb, Cs, Ca, Mg, Sr and Ba, a, b, c, d, e, f, g, h and i represent an atomic ratio of each element, and when a=12, b is from 0.01 to 20, c is from 0 to 20, d is from 0.001 to 15, e is from 0.001 to 20, f is from 0 to 20, g is from 0 to 10, h is from 0.001 to 10, and i is a numerical value determined by an oxidation state of each component.

In one exemplary embodiment of the present disclosure, the method for preparing a molybdenum-bismuth-based composite metal oxide includes preparing a catalyst suspension comprising a molybdenum-based compound; a bismuth-based compound; an $M^2$-based compound; an $M^3$-based compound; and an $M^6$-based compound. The catalyst suspension optionally further comprising one or more of: an $M^1$-based compound, an $M^4$-based compound, and an $M^5$-based compound. The catalyst suspension may be prepared by dissolving or dispersing the compounds in a solvent such as water.

In one exemplary embodiment of the present disclosure, the method for preparing a molybdenum-bismuth-based composite metal oxide includes drying the catalyst suspension. The drying is a step of evaporating water included in the catalyst suspension to form a solid. The method of drying is not particularly limited, and examples thereof may include a method of drying using a spray dryer, a method of drying using a slurry dryer, a method of drying using a drum dryer, a method of evaporation drying, a method of drying using an oven, and the like.

In one exemplary embodiment of the present disclosure, the drying of the catalyst suspension may be conducted at a temperature of 60° C. to 200° C. in air. The temperature may be adjusted to a temperature of 100° C. to 190° C. or a temperature of 120° C. to 180° C. When the temperature is lower than the above-mentioned temperature ranges, drying is not sufficiently conducted, and when the temperature is higher than the above-mentioned temperature ranges, the catalyst may be damaged.

In one exemplary embodiment of the present disclosure, the drying of the catalyst suspension may be conducted for a time of 1 h to 48 h. The time may be adjusted to a time of 5 h to 40 h or a time of 10 h to 30 h, where h means an hour. When the time is shorter than the above-mentioned time ranges, drying is not sufficiently conducted, and when the time is longer than the above-mentioned time ranges, the catalyst may be damaged.

In one exemplary embodiment of the present disclosure, the catalyst suspension may be dried by placing the catalyst suspension in an oven, and adjusting the temperature and the time.

In one exemplary embodiment of the present disclosure, any one or more of the molybdenum-based compound; the bismuth-based compound; the $M^2$-based compound; the $M^3$-based compound; and the $M^6$-based compound may be an oxide or hydrate of each element. The compound may be in a form of a precursor including each metal element, and by using the oxide or hydrate form, there is an advantage of minimizing nitric acid generation compared to using a nitric acid salt-type precursor, or minimizing ammonia generation compared to using an ammonium salt-type precursor.

In one exemplary embodiment of the present disclosure, the amount (g) or the number of moles (mol) of the generated nitric acid or ammonia may be calculated from the stoichiometric relationship between the nitric acid and the ammonia included in each metal precursor. For example, when using ammonium molybdate $\{(NH_4)_6(Mo_7O_{24})\cdot 4H_2O\}$ as the molybdenum-based compound, the amount (g) of generated ammonia may be calculated from the number of moles and the molecular weight of the ammonium molybdate. Specifically, the amount of ammonia (g)={mass of ammonium molybdate/molecular weight of ammonium molybdate}*{ratio of number of moles of ammonia included in ammonium molybdate}*(molecular weight of ammonia). Specifically, when using 1,000 g of ammonium molybdate $\{(NH_4)_6(Mo_7O_{24})\cdot 4H_2O\}$, the amount (g) of generated ammonia may be calculated as {(1,000 g)/(1235.9 g/mol)}*(6 mol/1 mol)*(18 g/mol)=87.39 g.

In one exemplary embodiment of the present disclosure, the oxide or hydrate means an oxide or hydrate form of each element.

In one exemplary embodiment of the present disclosure, any one or more of the molybdenum-based compound; the bismuth-based compound; the $M^2$-based compound; the $M^3$-based compound; and the $M^6$-based compound may be an oxide of each element.

In one exemplary embodiment of the present disclosure, the molybdenum-based compound may be molybdenum oxide ($MoO_3$).

In one exemplary embodiment of the present disclosure, the bismuth-based compound may be bismuth oxide ($Bi_2O_3$).

In one exemplary embodiment of the present disclosure, a total weight of the oxide or hydrate of each element of the molybdenum-based compound; the bismuth-based compound; the $M^2$-based compound; the $M^3$-based compound;

and the $M^6$-based compound may be greater than or equal to 1% by weight and less than or equal to 100% by weight based on a total weight of the catalyst suspension.

In one exemplary embodiment of the present disclosure, the catalyst suspension may further include salts of one or more metals selected from the group consisting of W, Sb, As, P, Sn, Pb, Al, Zr, V, Ce, Se, Ga, Ti, Ge, Rh and Au.

The method for preparing a molybdenum-bismuth-based composite metal oxide according to one exemplary embodiment of the present disclosure further includes pulverizing the molybdenum-bismuth-based composite metal oxide.

In one exemplary embodiment of the present disclosure, the molybdenum-bismuth-based composite metal oxide may be pulverized to an average particle diameter of 10 μm to 1,000 μm.

The method for preparing a molybdenum-bismuth-based composite metal oxide according to one exemplary embodiment of the present disclosure may further include mixing the molybdenum-bismuth-based composite metal oxide and a binder. The binder is introduced to improve strength and friction resistance of the catalyst.

In one exemplary embodiment of the present disclosure, an organic-based binder or an inorganic-based binder may be used as the binder. Examples of the organic-based binder may include polymer compounds such as polyvinyl alcohol, α-glucan derivatives, β-glucan derivatives and the like. These may be used singly or as a combination of two or more binders.

The α-glucan derivative represents, among polysaccharides formed with glucose, a polysaccharide in which glucose bonds in an α-type structure, and examples thereof may include derivatives such as α1-4 glucan, α1-6 glucan and α1-4/1-6 glucan. As such an α-glucan derivative, amylose, glycogen, amylopectin, pullulan, dextrin, cyclodextrin or the like may be specifically included. These may be used singly or as a combination of two or more binders.

The βglucan derivative represents, among polysaccharides formed with glucose, a polysaccharide in which glucose bonds in a β-type structure, and examples thereof may include derivatives such as β1-4 glucan, β1-3 glucan, β1-6 glucan and β1-3/1-6 glucan. Examples of such a β glucan derivative may include cellulose derivatives such as methylcellulose, ethylcellulose, carboxylmethylcellulose, carboxylmethylcellulose sodium, hydroxyethyl cellulose, hydroxypropyl cellulose, hydroxypropyl methylcellulose, hydroxyethyl methylcellulose, hydroxybutyl methylcellulose, ethyl hydroxyethyl cellulose and hydroxypropyl cellulose, β1-3 glucan such as curdlan, laminaran, paramylon, callose, pachyman and scleroglucan, and the like. These may be used in singly or as a combination of two or more types.

The organic-based binder may be used unpurified or purified, however, the content of metal impurities or ignition residues is preferably small to suppress decline of catalytic performance caused by metals as impurities or ignition residues.

Examples of the inorganic-based binder may include inert carriers including inorganic compounds such as silica, alumina, silica-alumina, silicon carbide, titania, magnesia, graphite and diatomite, ceramic balls, stainless steel, inorganic fibers such as glass fibers, ceramic fibers and carbon fibers, and the like. These may be used singly or as a combination of two or more binders. In addition, the organic-based binder and the inorganic-based binder may be mixed and used.

The amount of the binder used may be selected depending on the type or size of the catalyst precursor, the type of the liquid, and the like, however, the amount is preferably from 0.05 parts by mass to 15 parts by mass, more preferably from 0.1 parts by mass to 10 parts by mass, and even more preferably from 1 parts by mass to 8 parts by mass with respect to 100 parts by mass of the catalyst precursor.

In addition, an additive widely known as a powder binder such as ammonium nitrate, cellulose, starch, polyvinyl alcohol or steric acid may be used as the binder.

In one exemplary embodiment of the present disclosure, the catalyst suspension may include a solvent, and examples of the solvent may include water, ethyl alcohol, acetone and the like. These may be used singly or as a combination of two or more types. Among these, using water is preferred.

The method for preparing a molybdenum-bismuth-based composite metal oxide according to one exemplary embodiment of the present disclosure further includes placing the molybdenum-bismuth-based composite metal oxide in a carrier.

In one exemplary embodiment of the present disclosure, the placing of the molybdenum-bismuth-based composite metal oxide in a carrier may include a method of mixing the molybdenum-bismuth-based composite metal oxide and the carrier.

In one exemplary embodiment of the present disclosure, a material of the carrier is not particularly limited as long as it does not inhibit activity of the catalyst. Examples of the carrier may include one or more compounds selected from the group consisting of $SiO_2$, $Al_2O_3$, MgO, $MgCl_2$, $CaCl_2$, $ZrO_2$, $TiO_2$, $B_2O_3$, CaO, ZnO, BaO, $ThO_2$, $SiO_2$—$Al_2O_3$, $SiO_2$—MgO, $SiO_2$—$TiO_2$, $SiO_2$—$V_2O_5$, $SiO_2$—$CrO_2O_3$, $SiO_2$—$TiO_2$—MgO and zeolite.

The method for preparing a molybdenum-bismuth-based composite metal oxide according to one exemplary embodiment of the present disclosure may further include calcining the molybdenum-bismuth-based composite metal oxide.

In one exemplary embodiment of the present disclosure, a step of calcining for 1 hour to 10 hours at 300° C. to 600° C. may be further included. The calcination may be conducted under an inert gas or oxidation atmosphere (for example, mixed gas atmosphere of air or inert gas and oxygen), or, in addition thereto, a reduction atmosphere (for example, mixed gas atmosphere of inert gas, oxygen and $NH_3$, CO and/or $H_2$). In addition, the time of calcination may be from several minutes to several hours, and may be generally shortened as the temperature increases.

Hereinafter, preferred examples are provided to illuminate the present disclosure. However, the following examples are for illustrative purposes only, and the present disclosure is not limited thereto.

Example 1

To a 5 L reactor equipped with a stirrer, water (2,500 g) was introduced, then $MoO_3$ (815 g), $Bi_2O_3$ (165 g), $Fe_2O_3$ (56 g), CoO (194 g) and $K_2O$ (4.4 g) were introduced, and the result was mixed for 30 minutes to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (Cerakwool, silica-alumina fiber, manufactured by KCC Corporation) (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

The precursor material has an oxide form and does not include a nitric acid or ammonia component, and therefore, nitric acid and ammonia components generated from the precursor material were not present.

Example 2

To a 5 L reactor equipped with a stirrer, water (2,500 g) was introduced, and ammonium molybdate $\{(NH_4)_6(Mo_7O_{24})\cdot 4H_2O\}$ (1,000 g, 0.81 mol) was dissolved therein to prepare a solution.

To the solution, $Bi_2O_3$ (165 g), $Fe_2O_3$ (56 g), CoO (194 g) and $K_2O$ (4.4 g) were introduced, and the result was mixed for 30 minutes to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (Cerakwool, silica-alumina fiber, manufactured by KCC Corporation) (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

Herein, the amount (g) of ammonia ($NH_4$) generated from the ammonium molybdate $\{(NH_4)_6(Mo_7O_{24})\cdot 4H_2O\}$ was calculated as {(1,000 g)/(1235.9 g/mol)}*(6 mol/1 mol)*(18 g/mol)=87.39 g.

Example 3

To a 5 L reactor equipped with a stirrer, water (2,500 g) was introduced, and ammonium molybdate $\{(NH_4)6(Mo_7O_{24})\cdot 4H_2O\}$ (1,000 g) was dissolved therein to prepare a first solution.

Bismuth nitrate $\{Bi(NO_3)_3\cdot 5H_2O\}$ (343 g) and nitric acid (75 g) were dissolved in the solution to prepare a second solution.

The first solution and the second solution were mixed while maintaining the temperature at approximately 40° C., $Fe_2O_3$ (56 g), CoO (194 g) and $K_2O$ (4.4 g) were introduced thereto, and the result was mixed for 30 minutes to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

Herein, the amount (g) of ammonia ($NH_4$) generated from the ammonium molybdate $\{(NH_4)_6(Mo_7O_{24})\cdot 4H_2O\}$ was calculated as {(1,000 g)/(1235.9 g/mol)}*(6 mol/1 mol)*(18 g/mol)=87.39 g, the amount (g) of nitric acid ($HNO_3$) generated from the bismuth nitrate $\{Bi(NO_3)_3\cdot 5H_2O\}$ was calculated as {(343 g)/(485.11 g/mol)}*(3 mol/1 mol)*(63 g/mol)=133.63 g, and a total sum of the generated amounts of the ammonia and the nitric acid was 221.02 g.

Example 4

To a 5 L reactor equipped with a stirrer, water (2,500 g) was introduced, and ammonium molybdate $\{(NH_4)_6(Mo_7O_{24})\cdot 4H_2O\}$ (1,000 g) was dissolved therein while heating to 90° C. to prepare a first solution.

Bismuth nitrate $\{Bi(NO_3)_3\cdot 5H_2O\}$ (343 g), iron nitrate $\{Fe(NO_3)_3\cdot 9H_2O\}$ (286 g) and nitric acid (75 g) were dissolved in distilled water (500 ml) to prepare a second solution.

The first solution and the second solution were mixed while maintaining the temperature at approximately 40° C., CoO (194 g) and $K_2O$ (4.4 g) were introduced thereto, and the result was mixed for 30 minutes to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

Herein, the amount (g) of ammonia ($NH_4$) generated from the ammonium molybdate $\{(NH_4)_6(Mo_7O_{24})\ 4H_2O\}$ was calculated as {(1,000 g)/(1235.9 g/mol)}*(6 mol/1 mol)*(18 g/mol)=87.39 g, the amount (g) of nitric acid ($HNO_3$) generated from the bismuth nitrate $\{Bi(NO_3)_3\cdot 5H_2O\}$ was calculated as {(343 g)/(485.11 g/mol)}*(3 mol/1 mol)*(63 g/mol)=133.63 g, the amount (g) of nitric acid ($HNO_3$) generated from the iron nitrate $\{Fe(NO_3)_3\cdot 9H_2O\}$ was calculated as {(286 g)/(404.02 g/mol)}*(3 mol/1 mol)*(63 g/mol)=133.79 g, and a total sum of the generated amounts of the ammonia and the nitric acid was 354.81 g.

Example 5

To a 5 L reactor equipped with a stirrer, water (2,500 g) was introduced, and ammonium molybdate $\{(NH_4)_6(Mo_7O_{24})\cdot 4H_2O\}$ (1,000 g) was dissolved therein while heating to 90° C. to prepare a first solution.

Bismuth nitrate $\{Bi(NO_3)_3\cdot 5H_2O\}$ (343 g), cobalt nitrate $\{Co(NO_3)_2\cdot 6H_2O\}$ (755 g) and nitric acid (75 g) were dissolved in distilled water (500 ml) to prepare a second solution.

The first solution and the second solution were mixed while maintaining the temperature at approximately 40° C., $Fe_2O_3$ (56 g) and $K_2O$ (4.4 g) were introduced thereto, and the result was mixed for 30 minutes to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

Herein, the amount (g) of ammonia ($NH_4$) generated from the ammonium molybdate {$(NH_4)_6(Mo_7O_{24})\cdot 4H_2O$} was calculated as {(1,000 g)/(1235.9 g/mol)}*(6 mol/1 mol)*(18 g/mol)=87.39 g, the amount (g) of nitric acid ($HNO_3$) generated from the bismuth nitrate {$Bi(NO_3)_3\cdot 5H_2O$} was calculated as {(343 g)/(485.11 g/mol)}*(3 mol/1 mol)*(63 g/mol)=133.63 g, the amount (g) of nitric acid ($HNO_3$) generated from the cobalt nitrate {$Co(NO_3)_2\cdot 6H_2O$} was calculated as {(755 g)/(291.05 g/mol)}*(2 mol/1 mol)*(63 g/mol)=326.85 g, and a total sum of the generated amounts of the ammonia and the nitric acid was 547.87 g.

Comparative Example 1

To a 5 L reactor equipped with a stirrer, water (2,500 g) was introduced, and ammonium molybdate (1,000 g) was dissolved therein while heating to 90° C. to prepare a first solution.

Bismuth nitrate {$Bi(NO_3)_3\cdot 5H_2O$} (343 g), iron nitrate {$Fe(NO_3)_3\cdot 9H_2O$} (286 g), cobalt nitrate {$Co(NO_3)_2\cdot 6H_2O$} (755 g), potassium nitrate {$KNO_3$} (10 g) and nitric acid (75 g) were dissolved in distilled water (500 ml) to prepare a second solution.

The first solution and the second solution were mixed while maintaining the temperature at approximately 40° C. to prepare a suspension. The prepared suspension was introduced to a 160° C. electric oven, dried for 24 hours, and then pulverized to a particle diameter of approximately 200 μm.

To the pulverized powder, ammonium nitrate (130 g), an inorganic fiber (5 wt %), and a mixed solvent of water and alcohol (20 wt %) were introduced, and the result was re-mixed and then extrusion molded to a size of 5 mm. The molded catalyst was calcined by heat treating for 5 hours at a temperature of 500° C.

Among the active components of the catalyst, the composition ratio of the elements other than oxygen was identified to be $Mo_{12}Bi_{1.5}Fe_{1.5}Co_{5.5}K_{0.2}$.

Herein, the amount (g) of ammonia ($NH_4$) generated from the ammonium molybdate {$(NH_4)_6(Mo_7O_{24})\cdot 4H_2O$} was calculated as {(1,000 g)/(1235.9 g/mol)}*(6 mol/1 mol)*(18 g/mol)=87.39 g, the amount (g) of nitric acid ($HNO_3$) generated from the bismuth nitrate {$Bi(NO_3)_3\cdot 5H_2O$} was calculated as {(343 g)/(485.11 g/mol)}*(3 mol/1 mol)*(63 g/mol)=133.63 g, the amount (g) of nitric acid ($HNO_3$) generated from the iron nitrate {$Fe(NO_3)_3\cdot 9H_2O$} was calculated as {(286 g)/(404.02 g/mol)}*(3 mol/1 mol)*(63 g/mol)=133.63 g, the amount (g) of nitric acid ($HNO_3$) generated from the cobalt nitrate {$Co(NO_3)_2\cdot 6H_2O$} was calculated as {(755 g)/(291.05 g/mol)}*(2 mol/1 mol)*(63 g/mol)=326.85 g, the amount (g) of nitric acid ($HNO_3$) generated from the potassium nitrate {$KNO_3$} was calculated as {(10 g)/(101.11 g/mol)}*(1 mol/1 mol)*(63 g/mol)=6.23 g, and a total sum of the generated amounts of the ammonia and the nitric acid was 687.89 g.

Experimental Example: Catalytic Activity Test

A pilot scale shell-and-tube-type fixed bed reactor formed with a reaction tube made of steel having an inner diameter of 1 inch and a fixed bed filling section length of 3000 mm, and a shell (diameter 100 mm) covering the same and having a thermal medium flowing was prepared. A raw material mixture gas (propylene 7.5 vol %, oxygen 14 vol %, water vapor 18 vol %, inert nitrogen gas 60.5 vol %) was flowed at a space rate of 1400 $hr^{-1}$ to conduct a reaction under a reaction temperature of 310° C. For the gas passing through the reactor, the number of moles of each product was compared using a gas chromatography analyzer to calculate conversion ratio and selectivity.

Condition of Gas Chromatography Operation

- Instrument: Agilent 7890B Gas Chromatography system
- Column: Molecular sieve 5 A 2.1 mm (L.D)*2.0 M 80/100 mesh
- Plot Q 2.1 mm (I.D)*2.0 M 80/100 mesh
- WAX-DA 0.53 mm (I.D)*30 M*1 μm
- Solvent: 1,4-dioxane
- Column temperature: measured while raising the temperature from 50° C. to 200° C.

The conversion ratio of propylene and the selectivity of acrolein and acrylic acid were calculated, and the results are shown in Table 1.

Propylene conversion ratio (%)=[(number of moles of reacted propylene)/(number of moles of supplied propylene)]*100(%)

Acrolein+acrylic acid selectivity (%)=[(number of moles of produced acrolein+acrylic acid)/(number of moles of reacted propylene)]*100(%)

Rate of nitric acid and ammonia generation (%): {weight of generated nitric acid and ammonia (g)}/{total sum of initial precursor weight (g)}*100(%)

TABLE 1

| | Example 1 | Example 2 | Example 3 | Example 4 | Example 5 | Comparative Example 1 |
|---|---|---|---|---|---|---|
| Ratio of Oxide in Precursor | 100% | 29.55% | 15.93% | 10.86% | 2.78% | 0% |
| Rate of Nitric Acid, Ammonia Generation (%) | 0% | 6.16% | 13.84% | 19.42% | 25.38% | 28.73% |
| Propylene Conversion Ratio | 98.5% | 98.2% | 98.6% | 98.4% | 99.1% | 98.7% |
| Acrolein + Acrylic Acid Selectivity | 91.8% | 92.1% | 91.6% | 91.8% | 91.2% | 91.7% |

From the results, it was identified that, when preparing a catalyst using the method for preparing a catalyst of the present disclosure, generation of nitric acid and ammonia, which are hazardous substances, was minimized while having superior catalyst performance.

The invention claimed is:

1. A method for preparing a molybdenum-bismuth-based composite metal oxide, the method comprising:

preparing a catalyst suspension consisting essentially of a solvent and a precursor material of each metal element, wherein the solvent is selected from the group consisting of water, ethyl alcohol, acetone, and a combination thereof, and the precursor material of each metal element comprises a molybdenum-based compound, a bismuth-based compound, an $M^2$-based compound, an $M^3$-based compound, an $M^6$-based compound, and optionally an $M^1$-based compound, an $M^4$-based compound, and an $M^5$-based compound; and drying the catalyst suspension, wherein the $M^2$-based compound and the $M^6$-based compound are in an oxidate form, excluding any nitrate or ammonium salt, wherein the molybdenum-bismuth-based composite metal oxide is represented by Chemical Formula 1:

[Chemical Formula 1]

$$Mo_aBi_bM^1_cM^2_dM^3_eM^4_fM^5_gM^6_hO_i,$$

wherein in Chemical Formula 1,

Mo is molybdenum;

Bi is bismuth;

$M^1$ is one or more selected from the group consisting of W, Sb, As, P, Sn and Pb;

$M^2$ is one or more selected from the group consisting of Fe, Zn, Cr, Mn, Cu, Pd, Ag and Ru;

$M^3$ is one or more selected from the group consisting of Co, Cd, Ta, and Pt;

$M^4$ is one or more selected from the group consisting of Zr and V;

$M^5$ is one or more selected from the group consisting of Se, Ga, Ti, Ge, Rh and Au;

$M^6$ is one or more selected from the group consisting of Na, K, Li, Rb, Cs, Ca, Mg, Sr and Ba;

a, b, c, d, e, f, g, h and i represent an atomic ratio of each element;

wherein a=12, b is from 0.01 to 20, c is from 0 to 20, d is from 0.001 to 15, e is from 0.001 to 20, f is from 0 to 20, g is from 0 to 10, his from 0.001 to 10, and i is a numerical value determined by an oxidation state of each component, and wherein any one or more of the molybdenum-based compound, the bismuth-based compound, the $M^2$-based compound, the $M^3$-based compound, and the $M^6$-based compound is an oxide or hydrate of Mo, Bi, $M^2$, $M^3$ and $M^6$, respectively, and wherein any two or more of the $M^2$-based compound, the $M^3$-based compound, and the $M^6$-based compound are oxides of $M^2$, $M^3$, and $M^6$, respectively, and are not nitrates or ammonium salts.

2. The method of claim 1, wherein a total weight of the oxide or hydrate of Mo, Bi, $M^2$, $M^3$ and $M^6$ is greater than or equal to 1% by weight and less than or equal to 100% by weight based on a total weight of the catalyst suspension.

3. The method of claim 1, wherein the catalyst suspension further includes one or more salts of elements selected from the group consisting of W, Sb, As, P, Sn, Pb, Zr, V, Se, Ga, Ti, Ge, Rh and Au.

4. The method of claim 1, further comprising calcining the molybdenum-bismuth-based composite metal oxide.

5. A method for preparing (meth)acrylic acid using a fixed bed reactor including a front-end catalyst layer and a rear-end catalyst layer, the method comprising:

preparing (meth)acrolein, which comprises supplying an injection gas including a raw material gas, which includes propylene, isobutylene or a mixture thereof, and oxygen gas to the front-end catalyst layer, wherein the injection gas comprises a raw material gas and oxygen, and wherein the raw material gas comprises propylene, isobutylene or a mixture thereof; and preparing (meth)acrylic acid, which comprises supplying the (meth)acrolein to the rear-end catalyst layer, wherein the front-end catalyst layer or the rear-end catalyst layer comprises the molybdenum-bismuth-based composite metal oxide prepared using the preparation method of claim 1.

6. The method of claim 1, wherein the catalyst suspension comprises one or more of the $M^1$-based compound, the $M^4$-based compound, and the $M^5$-based compound.

* * * * *